United States Patent [19]
Anjur et al.

[11] Patent Number: 5,645,542
[45] Date of Patent: Jul. 8, 1997

[54] ELASTOMERIC ABSORBENT STRUCTURE

[75] Inventors: Sriram Padmanabhan Anjur; Ketan Narendra Shah, both of Appleton; Anthony John Wisneski, Kimberly, all of Wis.

[73] Assignee: Kimberly-Clark Worldwide, Inc., Neenah, Wis.

[21] Appl. No.: 366,066

[22] Filed: Dec. 29, 1994

[51] Int. Cl.⁶ .......................... A61F 13/15; A61F 13/20
[52] U.S. Cl. .................. 604/368; 604/367; 604/365; 604/370
[58] Field of Search .................. 604/358, 365–377, 604/385.1; 428/152, 282–284

[56] References Cited

U.S. PATENT DOCUMENTS

| | | | |
|---|---|---|---|
| 2,357,392 | 9/1944 | Francis, Jr. | 18/47.5 |
| 4,724,184 | 2/1988 | Killian et al. | 428/227 |
| 4,741,949 | 5/1988 | Morman et al. | 428/224 |
| 4,773,903 | 9/1988 | Weisman et al. | 604/368 |
| 4,803,117 | 2/1989 | Daponte | 428/228 |
| 4,822,668 | 4/1989 | Tanaka et al. | 428/283 |
| 4,865,596 | 9/1989 | Weisman et al. | 604/368 |
| 4,879,170 | 11/1989 | Radwanski et al. | 428/233 |
| 4,931,005 | 6/1990 | Tanaka et al. | 425/83.1 |
| 5,114,781 | 5/1992 | Morman | 428/198 |
| 5,149,335 | 9/1992 | Kellenberger et al. | 604/358 |
| 5,391,161 | 2/1995 | Hellgren et al. | 604/366 |

FOREIGN PATENT DOCUMENTS

| | | |
|---|---|---|
| 0 333 209 | 9/1989 | European Pat. Off. . |
| 0 333 212 | 9/1989 | European Pat. Off. . |
| 0 341 870 A2 | 11/1989 | European Pat. Off. . |
| 63-260555 | 10/1988 | Japan . |
| 1 362 666 | 8/1974 | United Kingdom . |
| WO9301785 | 2/1993 | WIPO . |

*Primary Examiner*—John G. Weiss
*Assistant Examiner*—David J. Cho
*Attorney, Agent, or Firm*—John R. Schenian

[57] ABSTRACT

Disclosed is an elastomeric absorbent structure containing wettable staple fiber and thermoplastic elastomeric fiber. The elastomeric absorbent structure exhibits improved elastic properties as compared to an otherwise essentially identical absorbent structure without any thermoplastic elastomeric fiber. Also disclosed is a disposable absorbent product containing such an elastomeric absorbent structure.

17 Claims, 2 Drawing Sheets

ELASTOMERIC ABSORBENT STRUCTURE

BACKGROUND OF THE INVENTION

1. Field of the Invention

The present invention relates to an elastomeric absorbent structure suitable for use in absorbent products. More particularly, the present invention relates to an elastomeric absorbent structure comprising wettable staple fiber and an thermoplastic elastomeric fiber.

2. Description of the Related Art

Disposable absorbent products currently enjoy widespread use in a large variety of applications. Typical disposable absorbent products include those such as diapers, adult incontinent products, and bed pads, catamenial devices such as sanitary napkins and tampons, and other products such as wipes, bibs, wound dressings, and surgical capes or drapes. Such disposable absorbent products are generally suited to absorb many liquids, such as water, saline, and synthetic urine, and body liquids such as urine, menses, and blood.

The purpose of disposable absorbent products is typically body waste management. In order to manage liquid body waste, the disposable absorbent product typically includes an absorbent structure that must generally be able to first uptake the liquid into the absorbent structure, then distribute the liquid within the absorbent structure, and then retain the liquid within the absorbent structure.

Typically, the absorbent structure and the disposable absorbent product are made of materials that do not easily stretch, particularly when under the forces that the absorbent structure and the disposable absorbent product typically encounter when in use. One problem resulting from the inability of the absorbent structure and the disposable absorbent product to easily stretch is that such structure or product does not conform well to the body of the wearer using the disposable absorbent product. This is a particular problem when the wearer of the disposable absorbent product is active and moving about. Such a lack of conformity to the body of the wearer generally results in the disposable absorbent product not being as comfortable to the wearer as desired. In addition, a lack of conformity to the body of the wearer generally results in the disposable absorbent product not being as efficient in uptaking, distributing, and retaining a liquid as the disposable absorbent product was designed to handle. Another problem resulting from the inability of the absorbent structure to easily stretch is that if too much stress is placed on the absorbent structure during use, the absorbent structure may break apart into pockets or bunches of material, causing discomfort to the wearer and reducing the efficiency of the absorbent structure.

SUMMARY OF THE INVENTION

It is desirable to produce an absorbent structure able to meet or exceed the performance characteristics of known absorbent structures. In particular, it is desired to produce an absorbent structure which is capable of stretching and conforming to the body of a wearer and yet which absorbent structure is able to rapidly absorb a discharged liquid under pressures typically encountered during use and to retain the absorbed liquid under pressures typically encountered during use. These and other related goals are achieved by an elastomeric absorbent structure comprising a wettable staple fiber and a thermoplastic elastomeric fiber, wherein the absorbent structure exhibits improved stretchability as compared to an otherwise essentially identical absorbent structure which does not comprise the thermoplastic elastomeric fiber.

In one embodiment of the present invention, an absorbent structure comprises from about 20 to about 80 weight percent wettable staple fiber and from greater than 20 to about 80 weight percent thermoplastic elastomeric fiber, wherein all weight percents are based on the total weight of the wettable staple fiber and the thermoplastic elastomeric fiber in the elastomeric absorbent structure. The elastomeric absorbent structure exhibits a Specific Liquid Saturated Retention Capacity value of at least about 5 grams of liquid absorbed to a gram of absorbent structure basis, a Maximum Stretch value in a dry condition that is greater than about 60 percent, a Maximum Stretch value in a 100 percent liquid saturated condition that is greater than about 150 percent, a Stretch Recovery value in a dry condition that is greater than about 70 percent, and a Stretch Recovery value in a 100 percent liquid saturated condition that is greater than about 75 percent.

In another aspect, it is desirable to provide a disposable absorbent product, such as an infant diaper, which product includes an elastomeric absorbent structure.

In one embodiment, this goal is achieved in an absorbent garment comprising a liquid-permeable topsheet, a backsheet, and an elastomeric absorbent structure positioned between the topsheet and the backsheet, wherein the elastomeric absorbent structure comprises a wettable staple fiber and an thermoplastic elastomeric fiber.

DETAILED DESCRIPTION OF THE PREFERRED EMBODIMENT

In one aspect, the present invention concerns an absorbent structure useful in a disposable absorbent product possessing improved, desirable elastic characteristics achievable by the careful selection and use of wettable staple fiber and a thermoplastic elastomeric fiber employed in forming such absorbent structures and disposable absorbent products.

As used herein, the term "staple fiber" is meant to refer to a natural fiber or a length cut from, for example, a manufactured filament. Such staple fibers are intended to act in the absorbent structure of the present invention as a temporary reservoir for liquid and also as a conduit for liquid distribution.

Suitably, the staple fibers used in the absorbent structures herein should range in length from about 0.1 to about 15 cm, and more suitably from about 0.2 to about 7 cm. Staple fibers of these size characteristics help to impart desirable bulk, liquid acquisition, liquid distribution and strength characteristics, and/or desirable flexibility and resilience properties to the absorbent structures of this invention.

A wide variety of staple fiber materials can be employed in the absorbent structures herein. Staple fibers useful in the present invention may be formed from natural or synthetic materials and may include cellulosic fibers such as wood pulp fibers and modified cellulose fibers, textile fibers such as cotton or rayon, and substantially nonabsorbent synthetic polymeric fibers.

For reasons of availability and cost, cellulosic fibers will frequently be preferred for use as the staple fiber component of the absorbent structures of this invention. Most preferred are wood pulp fibers. However, other cellulosic fiber materials, such as cotton fibers, may also be used as the staple fiber.

Another preferred type of staple fiber useful herein comprises substantially nonabsorbent, crimped synthetic polymeric fibers. The individual fibers of this type are in and of themselves substantially nonabsorbent. Thus, such fibers should be prepared from a synthetic polymer material which does not substantially swell or gel in the presence of liquids, such as urine or menses, typically encountered in disposable absorbent products. Suitable polymeric materials which may be used to prepare the desired staple fibers include polyesters, polyolefins, polyacrylics, polyamides, and polystyrenes. Suitably, staple fibers are made of polyethylene, polypropylene, or polyethylene terephthalate.

The staple fibers used herein may also be crimped in order for the resulting absorbent structure to have the desired resilience and resistance to bunching during use in absorbent products. Crimped staple fibers are those which have a continuous wavy, curvy or jagged character along their length. Fiber crimping of this sort is described more fully in U.S. Pat. No. 4,118,531, incorporated herein by reference.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

As used herein, the term "wettable" is meant to refer to a fiber which exhibits a liquid, such as water, synthetic urine, or a 0.9 weight percent aqueous saline solution, in air contact angle of less than 90°. As used herein, the contact angle may be determined, for example, as set forth by Robert J. Good and Robert J. Stromberg, Ed., in "Surface and Colloid Science—Experimental Methods", Vol. 11, (Plenum Press, 1979). Suitably, a wettable fiber refers to a fiber which exhibits a 0.9 weight percent aqueous saline solution in air contact angle of less than 90° at a temperature between about 0° C. and about 100° C. and suitably at ambient conditions, such as about 23° C.

Suitable wettable fibers may be formed from intrinsically wettable fibers or may be formed from intrinsically hydrophobic fibers having a surface treatment thereon which renders the fiber hydrophilic. When surface treated fibers are employed, the surface treatment is desirably nonfugitive. That is, the surface treatment desirably does not wash off the surface of the fiber with the first liquid insult or contact. For the purposes of this application, a surface treatment on a generally hydrophobic polymer will be considered to be nonfugitive when a majority of the fibers demonstrate a liquid in air contact angle of less than 90° for three consecutive contact angle measurements, with drying between each measurement. That is, the same fiber is subjected to three separate contact angle determinations and, if all three of the contact angle determinations indicate a contact angle of liquid in air of less than 90°, the surface treatment on the fiber will be considered to be nonfugitive. If the surface treatment is fugitive, the surface treatment will tend to wash off of the fiber during the first contact angle measurement, thus, exposing the hydrophobic surface of the underlying fiber and will demonstrate subsequent contact angle measurements greater than 90°.

The wettable staple fibers should be present in the elastomeric absorbent structure of the present invention in an amount effective to result in the desired absorbent and elastic properties described herein.

As such, the wettable staple fiber should be present in the absorbent structure in less than an excessive amount so that the absorbent structure exhibits the desired elastic properties. In addition, the wettable staple fiber should be present in the absorbent structure in more than a minimal amount so that the absorbent structure exhibits the desired absorbent properties.

The wettable staple fiber is therefore desirably present in an elastomeric absorbent structure of the present invention in an amount from about 20 to about 80 weight percent, suitably from about 25 to about 75 weight percent, and more suitably from about 30 to about 70 weight percent wettable staple fiber, with all weight percents based on the total weight of the wettable staple fiber and thermoplastic elastomeric fiber in the absorbent structure.

It has been found that by including a thermoplastic elastomeric fiber in an absorbent structure, the elastic properties of the absorbent structure may be substantially improved, particularly as compared to an otherwise essentially identical absorbent structure not comprising a thermoplastic elastomeric fiber.

In particular, the absorbent structures of the present invention have been found to exhibit very high elastic stretchability and very high elastic recovery from stretch, as compared to an otherwise essentially identical absorbent structure that does not comprise a thermoplastic elastomeric fiber.

As used herein, the term "otherwise essentially identical absorbent structure without any thermoplastic elastomeric fiber," and other similar terms, are intended to refer to a control absorbent structure that is prepared using essentially identical materials and an essentially identical process as compared to an elastomeric absorbent structure of the present invention, except that the control absorbent structure does not comprise or is not prepared with the thermoplastic elastomeric fiber described herein but, instead, comprises an amount of additional wettable staple fiber essentially identical to the amount of thermoplastic elastomeric fiber used in the elastomeric absorbent structure of the present invention. As such, the otherwise essentially identical absorbent structure without any thermoplastic elastomeric fiber and the elastomeric absorbent structure of the present invention will generally have essentially identical basis weights. As a result of not comprising the thermoplastic elastomeric fiber, the otherwise essentially identical absorbent structure generally will not exhibit the desired elastic properties described herein as compared to an elastomeric absorbent structure of the present invention.

As used herein, the term "thermoplastic" is meant to describe a material that softens when exposed to heat and which substantially returns to its original condition when cooled to room temperature.

As used herein, the terms "elastic" and "elastomeric" are used interchangeably to mean a material that is generally capable of recovering its shape after deformation when the deforming force is removed. Specifically, as used herein, elastic or elastomeric is meant to be that property of any material which, upon application of a biasing force, permits that material to be stretchable to a stretched, biased length which is at least about 125 percent, that is about 1.25 times, its relaxed, unbiased length, and that will cause the material to recover at least 40 percent of its elongation upon release of the stretching, elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, and many of these will recover to substantially their original relaxed length upon release of the stretching, elongating force. This latter class of materials is generally beneficial for purposes of the present invention.

The term "recover" relates to a contraction of a stretched material upon termination of a biasing force following stretching of the material by application of the biasing force. For example, if a material having a relaxed, unbiased length of one (1) inch were elongated 50 percent by stretching to a length of 1.5 inches, the material would have been elongated 50 percent and would have a stretched length that is 150 percent of its relaxed length. If this exemplary stretched material contracted, that is, recovered to a length of 1.1 inches after release of the biasing and stretching force, the material would have recovered 80 percent (0.4 inch) of its elongation.

Materials suitable for use in preparing the thermoplastic elastomeric fiber herein include diblock, triblock, or multi-block elastomeric copolymers such as olefinic copolymers such as styrene-isoprene-styrene, styrene-butadiene-styrene, styrene-ethylene/butylene-styrene, or styrene-ethylene/propylene-styrene, such as those available from the Shell Chemical Company, under the trade designation Kraton elastomeric resin; polyurethanes, such as those available from E. I. Du Pont de Nemours Co., under the trade name Lycra polyurethane; polyamides, such as polyether block amides available from Ato Chemical Company, under the trade name Pebax polyether block amide; or polyesters, such as those available from E. I. Du Pont de Nemours Co., under the trade name Hytrel polyester.

A number of block copolymers can be used to prepare the thermoplastic elastomeric fibers useful in this invention. Such block copolymers generally comprise an elastomeric midblock portion and a thermoplastic endblock portion. The block copolymers used in this invention generally have a three-dimensional physical crosslinked structure below the endblock portion glass transition temperature ($T_g$) and are elastomeric. The block copolymers are also thermoplastic in the sense that they can be melted above the endblock $T_g$, formed, and resolidified several times with little or no change in physical properties (assuming a minimum of oxidative degradation).

One way of synthesizing such block copolymers is to polymerize the thermoplastic endblock portions separately from the elastomeric midblock portions. Once the midblock and endblock portions have been separately formed, they can be linked. Typically, midblock portions can be obtained by polymerizing di- and tri-unsaturated $C_4$–$C_{10}$ hydrocarbons such as, for example, dienes such as butadiene, isoprene, and the like, and trienes such as 1,3,5-heptatriene, and the like. When an endblock portion A is joined to a midblock portion B, an A-B block copolymer unit is formed, which unit can be coupled by various techniques or with various coupling agents C to provide a structure such as A-B-A, which is believed to comprise two A-B blocks joined together in a tail-to-tail A-B-C-B-A arrangement. By a similar technique, a radial block copolymer can be formed having the formula $(A-B)_nC$, wherein C is the hub or central, polyfunctional coupling agent and n is a number greater than 2. Using the coupling agent technique, the functionality of C determines the number of A-B branches.

Endblock portion A generally comprises a poly (vinylarene), such as polystyrene, having an average molecular weight between 1,000 and 60,000. Midblock portion B generally comprises a substantially amorphous polyolefin such as polyisoprene, ethylene/propylene polymers, ethylene/butylene polymers, polybutadiene, and the like, or mixtures thereof, having an average molecular weight between about 5,000 and about 450,000. The total molecular weight of the block copolymer is suitably about 10,000 to about 500,000 and more suitably about 200,000 to about 300,000. Any residual unsaturation in the midblock portion of the block copolymer can be hydrogenated selectively so that the content of olefinic double bonds in the block copolymers can be reduced to a residual proportion of less than 5 percent and suitably less than about 2 percent. Such hydrogenation tends to reduce sensitivity to oxidative degradation and may have beneficial effects upon elastomeric properties.

Suitable block copolymers used in this invention comprise at least two substantially polystyrene endblock portions and at least one substantially ethylene/butylene midblock portion. As an example, ethylene/butylene typically may comprise the major amount of the repeating units in such a block copolymer and can constitute, for example, 70 percent by weight or more of the block copolymer. The block copolymer, if radial, can have three or more arms, and good results can be obtained with, for example, four, five, or six arms. The midblock portion can be hydrogenated, if desired.

Linear block copolymers, such as A-B-A, A-B-A-B-A, or the like, are suitably selected on the basis of endblock content, large endblocks being preferred. For polystyrene-ethylene/butylene-polystyrene block copolymers, a styrene content in excess of about 10 weight percent is suitable, such as between about 12 to about 30 weight percent. With higher styrene content, the polystyrene endblock portions generally have a relatively high molecular weight. A commercially available example of such a linear block copolymer is a styrene-ethylene/butylene-styrene block copolymer which contains about 13 weight percent styrene units, and essentially the balance being ethylene/butylene units, commercially available from the Shell Chemical Company, under the trade designation KRATON G1657 elastomeric resin. Typical properties of KRATON G1657 elastomeric resin are reported to include a tensile strength of 3400 pounds per square inch ($2\times10^6$ kilograms per square meter), a 300 percent modulus of 350 pounds per square inch ($1.4\times10^5$ kilograms per square meter), an elongation of 750 percent at break, a Shore A hardness of 65, and a Brookfield viscosity, when at a concentration of 25 weight percent in a toluene solution, of about 4200 centipoise at room temperature.

The thermoplastic elastomeric fiber may generally be formed from any thermoplastic elastomeric composition capable of extrusion into fibers. A suitable thermoplastic elastomeric fiber for the present invention comprises melt-blown fibers. Such meltblown fibers are typically very fine fibers prepared by extruding liquified, or melted, fiber-forming copolymer through orifices in a die into a high velocity gaseous stream. The fibers are attenuated by the gaseous stream and are subsequently solidified. The resulting stream of solidified thermoplastic elastomeric fibers can be collected as, for example, on a screen disposed in the gaseous stream, as an entangled coherent fibrous mass. Such an entangled fibrous mass is characterized by extreme entanglement of the fibers. This entanglement provides coherency and strength to the resulting web structure. Such entanglement also adapts the web structure to constrain or entrap the wettable staple fiber within the structure after the wettable staple fiber has been incorporated into the web structure, either during or after formation of the web structure. The thermoplastic elastomeric fibers are generally entangled sufficiently that it is generally impossible to remove one complete fiber from the mass of fibers or to trace one fiber from beginning to end.

As used herein, the constraining or entrapment of the wettable staple fiber within the web structure is meant to represent that the wettable staple fiber is substantially immobilized, such that the wettable staple fiber is not free to substantially move or migrate within or out of the web structure. Such constraining or entrapment may be, for example, by adhesive means or by the entanglement of the thermoplastic elastomeric fibers of the web structure.

The thermoplastic elastomeric fiber used herein may be circular but may also have other cross-sectional geometries such as elliptical, rectangular, triangular, or multi-lobal.

The thermoplastic elastomeric fiber is suitably wettable. The thermoplastic elastomeric fiber may be made wettable by first preparing the thermoplastic elastomeric fiber and then subsequently applying a hydrophilizing surface treatment to the fiber.

Alternatively, the thermoplastic elastomeric fiber is prepared comprising a hydrophilizing polymeric component. In general, any polymeric component capable of being polymerized with the thermoplastic elastomeric component, capable of hydrophilizing the resultant copolymeric material to render it wettable according to the definition of the present invention, wherein the hydrophilizing component does not substantially affect the elastic properties of the prepared fiber, is suitable for use in the present invention. Hydrophilizing polymeric components suitable for use in the present invention include polyethylene oxide or polyvinyl alcohol.

The thermoplastic elastomeric fiber should be present in the absorbent structure of the present invention in an amount effective to result in the desired absorbent and elastic properties described herein. In particular, the thermoplastic elastomeric fiber should be present in the absorbent structure of the present invention in more than a minimal amount effective to substantially increase the elasticity of the elastomeric absorbent structure. At the same time, the thermoplastic elastomeric fiber should be present in the elastomeric absorbent structure of the present invention in less than an excessive amount so that the liquid absorptive properties of the elastomeric absorbent structure are not substantially negatively affected.

The thermoplastic elastomeric fiber is therefore desirably present in an elastomeric absorbent structure of the present invention in an amount from about 20 to about 80 weight percent, suitably from about 25 to about 75 weight percent, and more suitably from about 30 to about 70 weight percent, with all weight percents based on the total weight of the wettable staple fiber and thermoplastic elastomeric fiber in the absorbent structure.

While the principal components of the elastomeric absorbent structure of the present invention have been described in the foregoing, such elastomeric absorbent structure is not limited thereto and can include other components not adversely effecting the desired absorbent and elastic properties of the elastomeric absorbent structure. Exemplary materials which could be used as additional components would include, without limitation, pigments, antioxidants, stabilizers, surfactants, waxes, flow promoters, particulates, binder fibers, and materials added to enhance processability of the components.

For example, in order to enhance the absorbent capacity of an absorbent structure, it is known to incorporate into the absorbent structure a hydrogel-forming polymeric material. The introduction of hydrogel-forming polymeric material into such an absorbent structure generally allows for the use of less wettable staple fiber, since the hydrogel-forming polymeric material generally has a higher liquid absorption capacity on a gram per gram basis than the wettable staple fiber. Moreover, such hydrogel-forming polymeric material is generally less pressure sensitive than wettable staple fiber. Thus, the use of the hydrogel-forming polymeric material generally allows for the production and use of a smaller, thinner disposable absorbent product. As such, the absorbent structure of the present invention may also optionally include a hydrogel-forming polymeric material.

As used herein, "hydrogel-forming polymeric material" is meant to refer to a high absorbency material commonly referred to as a superabsorbent material. Such high absorbency materials are generally capable of absorbing an amount of a liquid, such as synthetic urine, a 0.9 weight percent aqueous saline solution, or bodily fluids, such as menses, urine, or blood, at least about 10, suitably about 20, and up to about 100 times the weight of the superabsorbent material at the conditions under which the superabsorbent material is being used. Typical conditions include, for example, a temperature of between about 0° C. to about 100° C. and suitably ambient conditions, such as about 23° C. and about 30 to about 60 percent relative humidity. Upon absorption of the liquid, the superabsorbent material typically swells and forms a hydrogel.

The hydrogel-forming polymeric material may be formed from an organic hydrogel material which may include natural materials, such as agar, pectin, and guar gum, as well as synthetic materials, such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyridines. Other suitable hydrogel polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble yet water swellable. Crosslinking may, for example, be by irradiation or covalent, ionic, van der Waals, or hydrogen bonding. Suitable superabsorbent materials are typically available from various commercial vendors, such as The Dow Chemical Company, Hoechst Celanese, Allied Colloids Limited, or Stockhausen, Inc.

The hydrogel-forming polymeric material, employed in the absorbent structures or products of the present invention, suitably should be able to absorb a liquid under an applied load. For the purposes of this application, the ability of a hydrogel-forming polymeric material to absorb a liquid under an applied load, and thereby perform work, is quantified as the Absorbency Under Load (AUL) value. The AUL value is expressed as the amount (in grams) of an aqueous 0.9 weight percent sodium chloride solution which the hydrogel-forming polymeric material can absorb in about 60 minutes per gram of hydrogel-forming polymeric material under a load of about 0.3 pound per square inch (approximately 2.0 kilopascals) while restrained from swelling in the plane normal to the applied load. The hydrogel-forming polymeric material employed in the absorbent structures of the present invention suitably exhibit an AUL value of at least about 15, more suitably of at least about 20, and up to about 50 grams of liquid per gram of hydrogel-forming polymeric material. The method by which the AUL value may be determined is set forth, for example, in detail in U.S. Pat. No. 5,149,335 or U.S. Pat. No. 5,247,072, incorporated herein by reference.

Suitably, the hydrogel-forming polymeric material is in the form of particles which, in the unswollen state, have maximum cross-sectional diameters within the range of from about 50 micrometers to about 1000 micrometers, preferably within the range of from about 100 micrometers to about 800 micrometers, as determined by sieve analysis according to American Society for Testing and Materials (ASTM) test method D-1921. It is to be understood that the particles of hydrogel-forming polymeric material falling within the ranges described above may comprise solid particles, porous particles, or may be agglomerated particles comprising many smaller particles agglomerated into particles falling within the described size ranges. The hydrogel-forming polymeric material is typically present in an absorbent structure or disposable absorbent product of the present invention in an amount effective to result in the absorbent structure or product being able to absorb a desired amount of liquid. The hydrogel-forming polymeric material is beneficially present in an absorbent structure in an amount of from about 15 to about 60 weight percent, suitably in an amount of from about 20 to about 50 weight percent, and more suitably of from about 25 to about 40 weight percent, based on the total weight of the hydrogel-forming polymeric material, wettable staple fiber, and thermoplastic elastomeric fiber in the absorbent structure.

Because the hydrogel-forming polymeric material present in the elastomeric absorbent structure of the present invention can be present in high concentrations, the elastomeric absorbent structures of the present invention can be relatively thin and light weight, have a relatively small volume, and still function in a desirable manner.

The elastomeric absorbent structure of the present invention suitably comprises a fibrous matrix comprising the thermoplastic elastomeric fiber wherein the fibrous matrix constrains or entraps the wettable staple fiber and, optionally, a hydrogel-forming polymeric material.

The fibrous matrix may be formed by air-laying fibers, through a spunbond or meltblown process, a carding process, a wet-laid process, or through essentially any other means, known to those skilled in the art, for forming a fibrous matrix.

Methods of incorporating the wettable staple fiber and, optionally, a hydrogel-forming polymeric material into the fibrous matrix are known to those skilled in the art. Suitable methods include incorporating the wettable staple fiber and, optionally, a hydrogel-forming polymeric material into the matrix during formation of the matrix, such as by air laying the fibers of the fibrous matrix and the wettable staple fiber and/or a hydrogel-forming polymeric material at the same time or wet-laying the fibers of the fibrous matrix and the wettable staple fiber and/or a hydrogel-forming polymeric material at the same time. Alternatively, it is possible to apply the wettable staple fiber and/or a hydrogel-forming polymeric material to the fibrous matrix after formation of the fibrous matrix. Other methods include sandwiching the hydrogel-forming polymeric material between two sheets of material, at least one of which is fibrous and liquid permeable. The hydrogel-forming polymeric material may be generally uniformly located between the two sheets of material or may be located in discrete pockets formed by the two sheets. It is preferable that the wettable staple fiber be generally uniformly distributed within the fibrous matrix. However, the wettable staple fiber may be nonuniformly distributed as long as the desired liquid absorptive properties and elastic properties of the elastomeric absorbent structure are still achieved.

The fibrous matrix may be in the form of a single, integrally formed layer or of a composite comprising multiple layers. If the fibrous matrix comprises multiple layers, the layers are preferably in liquid communication with one another, such that, a liquid present in one fibrous layer can flow or be transported to the other fibrous layer. For example, the fibrous layers may be separated by cellulosic tissue wrap sheets known to those skilled in the art.

The hydrogel-forming polymeric material may be distributed in the individual layers in a generally uniform manner or may be present in the fibrous layers as a layer or other nonuniform distribution.

The elastomeric absorbent structure of the present invention may generally be of any size or dimension as long as the elastomeric absorbent structure exhibits the desired absorbent and elastic characteristics as described herein. Typically, the elastomeric absorbent structure will have a volume of at least about 18 cubic centimeters, such as with a width of about 6 centimeters, a length of about 6 centimeters, and a depth of about 0.5 centimeter. Suitably, the elastomeric absorbent structure will have a volume of at least about 60 cubic centimeters, such as with a width of about 10 centimeters, a length of about 6 centimeters, and a depth of about 1 centimeter.

The elastomeric absorbent structure of the present invention suitably has a basis weight of about 100 grams per square meter (g/sm) to about 1000 g/sm, more suitably of about 200 g/sm to about 800 g/sm, and most suitably of about 300 g/sm to about 700 g/sm.

The elastomeric absorbent structure of the present invention suitably have a density of about 0.03 gram per cubic centimeter (g/cc) to about 0.5 g/cc, more suitably of about 0.05 g/cc to about 0.45 g/cc, and most suitably of about 0.08 g/cc to about 0.4 g/cc.

The elastomeric absorbent structure of the present invention may also be used or combined with other absorbent structures, with the elastomeric absorbent structure of the present invention being used as a separate layer or as an individual zone or area within a larger, composite absorbent structure. The elastomeric absorbent structure of the present invention may be combined with other absorbent structures by methods well known to those skilled in the art, such as by using adhesives or simply by layering the different structures together and holding together the composite structures with, for example, a tissue wrap sheet.

The elastomeric absorbent structure according to the present invention are suited to absorb many liquids, such as water, saline, and synthetic urine, and body liquids such as urine, menses, and blood, and are suited for use in disposable absorbent products such as diapers, adult incontinent products, and bed pads; in catamenial devices such as sanitary napkins, and tampons; and in other disposable absorbent products such as wipes, bibs, wound dressings, and surgical capes or drapes. Accordingly, in another aspect, the present invention relates to a disposable absorbent product comprising an elastomeric absorbent structure as described herein.

Use of the described elastomeric absorbent structure in a disposable absorbent product allows for the formation of a disposable absorbent product which is able to rapidly receive a discharged liquid and, yet, which disposable absorbent product is thin and which disposable absorbent product has desired elastic properties.

In one embodiment of the present invention, a disposable absorbent product is provided, which disposable absorbent product comprises a liquid-permeable topsheet, a backsheet attached to the topsheet, and an elastomeric absorbent structure positioned between the topsheet and the backsheet.

While one embodiment of the invention will be described in terms of the use of an elastomeric absorbent structure in an infant diaper, it is to be understood that the elastomeric absorbent structure is equally suited for use in other disposable absorbent products known to those skilled in the art.

Figure 1:
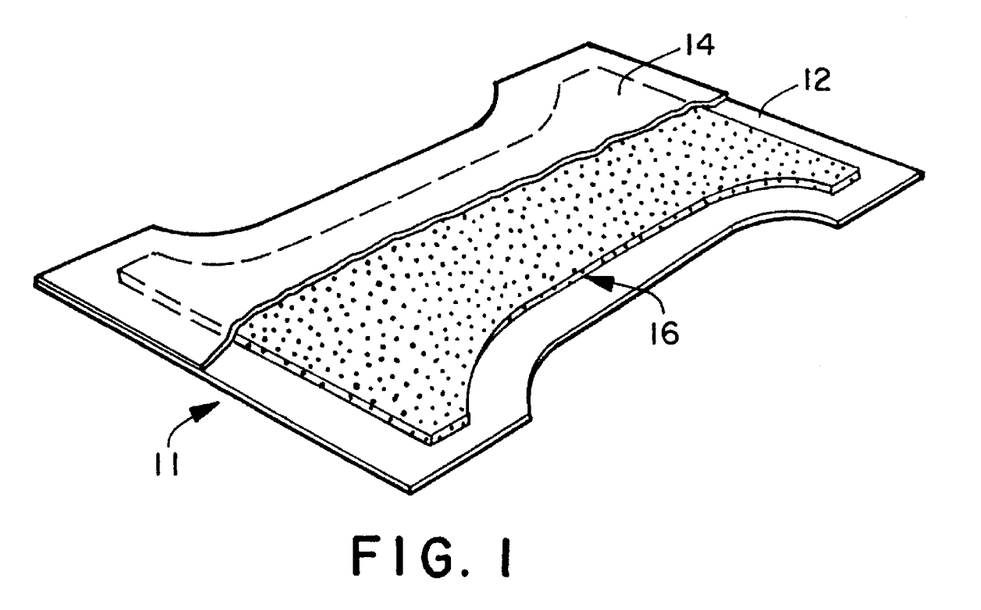
FIG. 1 is a perspective view of one embodiment of a disposable absorbent product according to the present invention.

Turning now to the drawing, FIG. 1 illustrates a disposable diaper 11 according to one embodiment of the present invention. Disposable diaper 11 includes a backsheet 12, a topsheet 14, and an elastomeric absorbent structure 16, located between the backsheet 12 and the topsheet 14. Elastomeric absorbent structure 16 is an absorbent structure according to the present invention.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

It is desirable that the elastomeric absorbent structure of the present invention exhibit both desirable elastic properties and desirable liquid absorptive properties.

Liquid absorptive properties desired of the elastomeric absorbent structure of the present invention include exhibiting an effective specific liquid saturated retention capacity.

As used herein, the "specific liquid saturated retention capacity" of an absorbent structure is meant to represent the amount of liquid the absorbent structure can retain, on a gram of liquid per gram of absorbent structure basis, when given a sufficient amount of time to reach 100 percent saturation with a 0.9 weight percent aqueous saline solution at room temperature and when an externally applied pressure of about 0.5 psi is applied to the saturated structure. The specific liquid saturated retention capacity of an absorbent structure may be determined according to the procedure described in the Test Methods section herein.

The elastomeric absorbent structure of the present invention suitably has a Specific Liquid Saturated Retention Capacity value, on a gram of liquid absorbed to a gram of absorbent structure basis (g/g), of at least about 5 g/g, suitably of at least about 7 g/g, more suitably of at least about 9 g/g, most suitably of at least about 11 g/g, and up to about 50 g/g.

An absorbent structure, in the form of a disposable absorbent product, will generally be worn by a wearer in both a dry and liquid saturated condition. As such, it is generally desired that the absorbent structure exhibit effective elastic properties in both a dry and a 100 percent liquid saturated condition. Thus, elastic properties desired of the elastomeric absorbent structure of the present invention include exhibiting effective maximum stretch in both a dry condition as well as a 100 percent liquid saturated condition and an effective stretch recovery in both a dry condition as well as a 100 percent liquid saturated condition.

The "maximum stretch" of a material is meant to represent the amount of stretch or extension a material may exhibit before the material breaks or, in other words, cohesively fails. As used herein, all stretching or extensions are expressed as a percent of the unextended or relaxed length of a material. Thus, 100 percent stretch or extension means that the untensioned material has been stretched to twice its relaxed, or untensioned, length. The maximum stretch of a material may be determined according to the test methods described herein.

A material will often exhibit a different maximum stretch value when in a dry condition as compared to when the material is in a 100 percent liquid saturated condition. This is because the liquid saturating the material will often interact with the material and affect the elastic properties of the material. As will be recognized by one skilled in the art, such a difference in the maximum stretch values for a material when in a dry condition as compared to when the material is in a 100 percent liquid saturated condition will depend on the composition and structure of the material.

As will be appreciated by one skilled in the art, a material such as an absorbent structure may entrap a relatively minor amount of liquid, such as water, within the material prior to use. For example, such liquid may be absorbed by the absorbent structure from humidity in the air. Such an absorbent structure is still intended to be considered in a dry condition for purposes of the present invention. Thus, as used herein, the "dry condition" of a material is meant to represent that the material comprises an amount of liquid that is suitably less than about 5 weight percent, more suitably less than about 3 weight percent, and most suitably less than about 1 weight percent, based on the total weight of the material.

As used herein, the "100 percent liquid saturated condition" of a material is meant to represent that the material comprises an amount of liquid that is about 100 percent of the absolute liquid saturated retention capacity of the material.

It is desired that the elastomeric absorbent structure of the present invention not exhibit a maximum stretch value, in either a dry condition or in a 100 percent liquid saturated condition, that is too low since such will indicate that the elastomeric absorbent structure is not sufficiently elastic.

Thus, the elastomeric absorbent structure of the present invention exhibits a Maximum Stretch value in a dry condition that is greater than about 60 percent, beneficially greater than about 80 percent, suitably greater than about 100 percent, more suitably greater than about 120 percent, and most suitably greater than about 140 percent.

The elastomeric absorbent structure of the present invention also exhibits a Maximum Stretch value in a 100 percent liquid saturated condition that is greater than about 150 percent, suitably greater than about 200 percent, more suitably greater than about 250 percent, and most suitably greater than about 300 percent.

In one embodiment of the present invention, the elastomeric absorbent structure exhibits a maximum stretch value in a 100 percent liquid saturated condition that is greater than the maximum stretch value exhibited by the elastomeric absorbent structure in a dry condition. This is believed to occur because the liquid saturating the elastomeric absorbent structure helps to break any hydrogen bonding that occurs among the wettable staple fibers, thereby improving the elastic properties of the elastomeric absorbent structure.

The "stretch recovery" of a material is meant to represent the amount of recovery a material exhibits upon termination of a biasing force following stretching of the material by application of the biasing force. As used herein, all stretch recovery values are expressed as the percent of an elongated portion of the length that the material recovers after being allowed to relax. As used herein, all stretch recovery values are meant to be determined when a material is elongated about 20 percent for about 20 minutes and then allowed to relax. For example, if a material having a relaxed, unbiased length of one (1) inch were elongated 20 percent by stretching to a length of 1.2 inches, the material would have been elongated 20 percent and would have a stretched length that is 120 percent of its relaxed length. If this exemplary stretched material contracted, that is, recovered to a length of 1.04 inches after release of the biasing and stretching force, the material would have a stretch recovery of 80 percent, having recovered 80 percent (0.16 inch) of its elongation. The stretch recovery of a material may be determined according to the test methods described herein.

The elastomeric absorbent structure of the present invention exhibits a Stretch Recovery value in a dry condition that is greater than about 70 percent, suitably greater than about 75 percent, more suitably greater than about 80 percent, and most suitably greater than about 90 percent.

The elastomeric absorbent structure of the present invention also exhibits a Stretch Recovery value in a 100 percent liquid saturated condition that is greater than about 75 percent, suitably greater than about 80 percent, more suitably greater than about 85 percent, and most suitably greater than about 90 percent.

TEST METHODS

Liquid Saturated Retention Capacity

Figure 2:
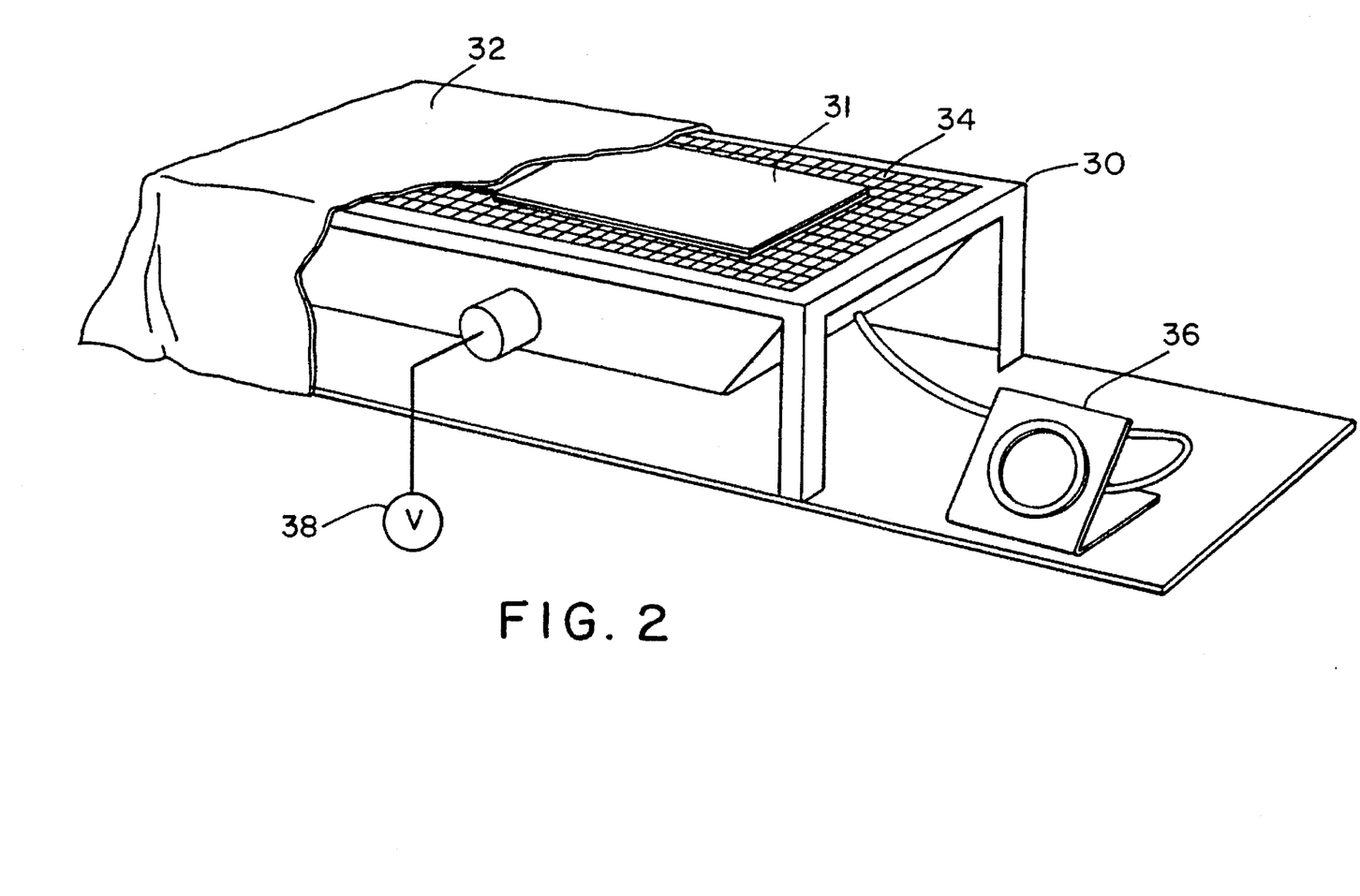
FIG. 2 is an illustration of the equipment employed in determining the liquid saturated retention capacity of a material.

The liquid saturated retention capacity is determined as follows. The material to be tested, having a moisture content of less than about 7 weight percent, is weighed and submerged in an excess quantity of a 0.9 weight percent aqueous saline solution at room temperature (about 23° C.). The material to be tested is allowed to remain submerged for about 20 minutes. After the 20 minute submerging, the material 31 is removed and, referring to FIG. 2, placed on a TEFLON™ coated fiberglass screen 34 having 0.25 inch (0.6 cm) openings (commercially available from Taconic Plastics Inc., Petersburg, N.Y.) which, in turn, is placed on a vacuum box 30 and covered with a flexible rubber dam material 32. A vacuum of about 0.5 pound per square inch (about 3.5 kilopascals) is drawn on the vacuum box for a period of about 5 minutes with the use of, for example, a vacuum gauge 36 and a vacuum pump (38). The material being tested is then removed from the screen and weighed. The amount of liquid retained by the material being tested is determined by subtracting the dry weight of the material from the wet weight of the material (after application of the vacuum), and is reported as the absolute liquid saturated retention capacity in grams of liquid retained. If desired, the weight of liquid retained may be converted to liquid volume by using the density of the test liquid, and is reported as the absolute liquid saturated retention capacity in milliliters of liquid retained. For relative comparisons, this absolute liquid saturated retention capacity value can be divided by the weight of the material 31 to give the specific liquid saturated retention capacity in grams of liquid retained per gram of tested material. This is reported as the Specific Liquid Saturated Retention Capacity value. If material, such as hydrogel-forming polymeric material or fiber, is drawn through the fiberglass screen while on the vacuum box, a screen having smaller openings should be used. Alternatively, a piece of tea bag or similar material can be placed between the material and the screen and the final value adjusted for the liquid retained by the tea bag or similar material.

Maximum Stretch

The maximum stretch of a material is evaluated by using a tensile tester, such as a Model 4201 Instron with Microcon II from the Instron Corporation, Canton Mass. The machine is calibrated by placing a 100 gram weight in the center of the upper jaw, perpendicular to the jaw and hanging unobstructed. The tension cell used is a 5 kilogram electrically-calibrating self-identifying load cell. The weight is then displayed on the Microcon display window. The procedure is performed in a room with standard-condition atmosphere such as about a temperature of about 23° C. and a relative humidity of about 50 percent.

A rectangular sample with a width of about 1 inch, a length of about 3 inches, a thickness of about 0.1 inch, and a basis weight of between about 300 to about 700 grams per square meter is weighed and pressure is applied to the sample to reach a desired density. The sample is then placed in the pneumatic action grips (jaws) with 1 inch by 3 inch rubber coated grip faces. The gauge length (the length of the sample actually being stretched) is about 2 inches and the crosshead speed is about 120 inches per minute. The crosshead speed is the rate at which the upper grip moves upward pulling the sample until failure. The maximum travel of the grips is about 14 inches. The maximum stretch is the stretched length of the material at failure, recorded as a percent of the original length (2 inches) of the untensioned sample. The maximum stretch is evaluated for the material in both a dry condition and a 100 percent liquid saturated condition. The maximum stretch for the material in a 100 percent liquid saturated condition is done by placing a dry sample in the jaws of the tester and then wetting the sample with a desired amount of 0.9% saline solution, as determined by the absolute liquid saturated retention capacity of the material. A time of 10 minutes is allowed for the sample to equilibrate.

Stretch Recovery

The stretch recovery of a material is evaluated by using a tensile tester, such as a Model 4201 Instron with Microcon II from the Instron Corporation, Canton Mass. The machine is calibrated by placing a 100 gram weight in the center of the upper jaw, perpendicular to the jaw and hanging unobstructed. The tension cell used is a 5 kilogram electrically-calibrating self-identifying load cell. The weight is then displayed on the Microcon display window. The procedure is performed in a room with standard-condition atmosphere such as about a temperature of about 23° C. and a relative humidity of about 50 percent.

A rectangular sample with a width of about 1 inch and a length of about 3 inches is weighed and pressure is applied to the sample to reach a desired density. The sample is then placed in the pneumatic action grips (jaws) with 1 inch by 3 inch rubber coated grip faces. The gauge length (the length of the sample actually being stretched) is about 2 inches and the crosshead speed is about 300 millimeters per minute. The crosshead speed is the rate at which the upper grip moves upward pulling the sample until failure. The sample is elongated about 20 percent, or about 0.4 inch, to a stretched gauge length of about 2.4 inches. The sample is maintained at this stretched length for about 20 minutes and then allowed to relax by removing the sample from the grips. The stretch recovery value is the final relaxed length minus the original length (2 inches), divided by the original length (2 inches), and multiplied by 100 percent. The stretch recovery is evaluated for the material in both a dry condition and a 100 percent liquid saturated condition. The stretch recovery for the material in a 100 percent liquid saturated condition is done by placing a dry sample in the jaws of the tester and then wetting the sample with a desired amount of 0.9% saline solution, as determined by the absolute liquid saturated retention capacity of the material. A time of 10 minutes is allowed for the sample to equilibrate.

EXAMPLE

Samples 1-3 are absorbent structures prepared comprising a wettable staple fiber and a thermoplastic elastomeric fiber. For the wettable staple fiber, a cellulosic wood pulp fluff, prepared from about 80 percent southern softwood and about 20 percent hardwood, was used.

For the thermoplastic elastomeric fiber, a block copolymer was prepared comprising about 75 weight percent of a styrene-ethylene/butylene-styrene block copolymer which contains about 13 weight percent styrene units, and essentially the balance being ethylene/butylene units, commercially available from the Shell Chemical Company, under the trade designation KRATON G1657 elastomeric resin, about 25 weight percent of a processing aid that was a polyethylene wax, commercially available from the Quantum Chemical Company, under the trade designation NA 601 and having a meltflow index of about 2000 grams per 10 minutes. These materials were mixed together before being extruded into a fiber with an average diameter of about 5 to about 30 micrometers.

The thermoplastic elastomeric fiber was meltblown into an entangled composite web with the hydrogel-forming polymeric material fed into the meltblown stream and the staple fiber fed into the composite web structure with a picker roll. After formation of the thermoplastic elastomeric fibers, a wetting agent was applied to the fibers. The wetting agent was octylphenoxypolyethoxyethanol nonionic surfactant, available from the Rohm & Haas Company, under the trade designation Triton X-102 surfactant.

Sample 4 was a control sample comprising a hydrogel-forming polymeric material and a wettable staple fiber. For the hydrogel-forming polymeric material, a poly(acrylic acid) high-absorbency material available from Stockhausen, Inc. under the designation Favor SAB 870, was used. For the wettable staple fiber, the same cellulosic wood pulp fluff as used in Sample 1-3 was used. Sample 4 was prepared by an airforming process where the wettable staple fibers and the hydrogel-forming polymeric material were mixed by an air stream and then airlaid into a web on top of a vacuum box. The composite web formed was then wrapped with a light basis weight tissue paper to allow for handling and testing of the sample.

The absolute and relative basis weight amounts used of the different materials for various samples is indicated in Table 1. The basis weight amounts are given in grams per square meter (g/sm) of absorbent structure formed. The initial dry density of each sample material was about 0.17 grams per cubic centimeter.

The samples were evaluated for maximum stretch and stretch recovery according to the procedures described herein. The results are described in Table 2. For some of the samples, exact measurements could not be made of the maximum stretch and stretch recovery values although the values were ascertained as being greater than or less than specific values.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

TABLE 1

| Sample No. | Thermoplastic Elastomeric Fiber Basis Weight (g/sm) | % | Hydrogel Basis Weight (g/sm) | % | Staple Fiber Basis Weight (g/sm) | % | Total Basis (g/sm) |
|---|---|---|---|---|---|---|---|
| 1* | 181 | 31 | 0 | 0 | 404 | 69 | 585 |
| 2 | 269 | 46 | 0 | 0 | 316 | 54 | 585 |
| 3 | 357 | 61 | 0 | 0 | 228 | 39 | 585 |
| 4* | 0 | 0 | 315 | 35 | 585 | 65 | 900 |

*Not an example of the present invention.

TABLE 2

| Sample No. | Maximum Stretch (percent) | | Stretch Recovery (Percent) | |
|---|---|---|---|---|
| | Dry | Saturated | Dry | Saturated |
| 1* | 30 | 90 | >80 | >90 |
| 2 | 160 | >300 | >80 | >90 |
| 3 | 175 | >300 | >80 | >90 |
| 4* | <5 | <5 | 0 | >90 |

*Not an example of the present invention.

What is claimed is:

1. An elastomeric absorbent structure comprising:
   a. from about 35 to about 65 weight percent wettable staple fiber; and
   b. from greater than about 35 to about 65 weight percent thermoplastic elastomeric fiber;

wherein all weight percents are based on the total weight of the wettable staple fiber and the thermoplastic elastomeric fiber in the elastomeric absorbent structure, and wherein the elastomeric absorbent structure exhibits the following properties:
   i. a Specific Liquid Saturated Retention Capacity value of at least about 5 grams of liquid absorbed to a gram of absorbent structure basis;
   ii. a Maximum Stretch value in a dry condition that is greater than about 60 percent;
   iii. a Maximum Stretch value in a 100 percent liquid saturated condition that is greater than about 150 percent;
   iv. a Stretch Recovery value in a dry condition that is greater than about 70 percent; and
   v. a Stretch Recovery value in a 100 percent liquid saturated condition that is greater than about 75 percent.

2. The elastomeric absorbent structure of claim 1 wherein the wettable staple fiber has a fiber length from about 0.1 to about 15 centimeters.

3. The elastomeric absorbent structure of claim 1 wherein the wettable staple fiber is selected from the group consisting of cellulosic fibers, textile fibers, and synthetic polymeric fibers.

4. The elastomeric absorbent structure of claim 1 wherein the wettable staple fiber is wood pulp fiber.

5. The elastomeric absorbent structure of claim 1 wherein the thermoplastic elastomeric fiber is a meltblown fiber comprising a block copolymer.

6. The elastomeric absorbent structure of claim 1 wherein the thermoplastic elastomeric fiber is wettable.

7. The elastomeric absorbent structure of claim 1 wherein the elastomeric absorbent structure exhibits Specific Liquid Saturated Retention Capacity value of at least about 7 grams of liquid absorbed to a gram of absorbent structure basis.

8. The elastomeric absorbent structure of claim 1 wherein the elastomeric absorbent structure exhibits a Maximum Stretch value in a dry condition that is greater than about 100 percent.

9. The elastomeric absorbent structure of claim 1 wherein the elastomeric absorbent structure exhibits a Maximum Stretch value in a 100 percent liquid saturated condition that is greater than about 200 percent.

10. The elastomeric absorbent structure of claim 1 wherein the elastomeric absorbent structure exhibits a Stretch Recovery value in a dry condition that is greater than about 75 percent.

11. The elastomeric absorbent structure of claim 1 wherein the elastomeric absorbent structure exhibits a Stretch Recovery value in a 100 percent liquid saturated condition that is greater than about 80 percent.

12. The elastomeric absorbent structure of claim 1 further comprising a hydrogel-forming polymeric material.

13. The elastomeric absorbent structure of claim 12 comprising from about 15 to about 60 weight percent of the hydrogel-forming polymeric material, based on the total weight of the hydrogel-forming polymeric material, the wettable staple fiber, and the thermoplastic elastomeric fiber in the elastomeric absorbent structure.

14. The elastomeric absorbent structure of claim 12 wherein the hydrogel-forming polymeric material is a polyacrylate material.

15. The elastomeric absorbent structure of claim 12 wherein the elastomeric absorbent structure comprises a fibrous matrix comprising the thermoplastic elastomeric fiber, wherein the fibrous matrix constrains the wettable staple fiber and the hydrogel-forming polymeric material.

16. An elastomeric absorbent structure comprising:
 a. from about 35 to about 65 weight percent wettable wood pulp fiber; and
 b. from about 35 to about 65 weight percent wettable thermoplastic elastomeric meltblown fiber comprising a polyolefin;

wherein all weight percents are based on the total weight of the wettable wood pulp fiber, and the wettable thermoplastic elastomeric meltblown fiber comprising a polyolefin in the absorbent structure, wherein the absorbent structure exhibits the following properties:
 i. a Specific Liquid Saturated Retention Capacity value of at least about 7 grams of liquid absorbed to a gram of absorbent structure basis;
 ii. a Maximum Stretch value in a dry condition that is greater than about 100 percent;
 iii. a Maximum Stretch value in a 100 percent liquid saturated condition that is greater than about 200 percent;
 iv. a Stretch Recovery value in a dry condition that is greater than about 75 percent; and
 v. a Stretch Recovery value in a 100 percent liquid saturated condition that is greater than about 80 percent.

17. A disposable absorbent product comprising:
a liquid permeable topsheet, a backsheet, and an elastomeric absorbent structure positioned between the topsheet and the backsheet, wherein the elastomeric absorbent structure comprises:
 a. from about 35 to about 65 weight percent wettable staple fiber; and
 b. from greater than about 35 to about 65 weight percent thermoplastic elastomeric fiber;

wherein all weight percents are based on the total weight of the wettable staple fiber and the thermoplastic elastomeric fiber in the elastomeric absorbent structure, and wherein the elastomeric absorbent structure exhibits the following properties:
 i. a Specific Liquid Saturated Retention Capacity value of at least about 5 grams of liquid absorbed to a gram of absorbent structure basis;
 ii. a Maximum Stretch value in a dry condition that is greater than about 60 percent;
 iii. a Maximum Stretch value in a 100 percent liquid saturated condition that is greater than about 150 percent;
 iv. a Stretch Recovery value in a dry condition that is greater than about 70 percent; and
 v. a Stretch Recovery value in a 100 percent liquid saturated condition that is greater than about 75 percent.

* * * * *